United States Patent
Aharoni et al.

(10) Patent No.: US 6,972,032 B2
(45) Date of Patent: Dec. 6, 2005

(54) INTRAOCULAR LENS IMPLANT

(75) Inventors: Eli Aharoni, Rishon le Zion (IL); Gideon Dotan, Yehud (IL); Yossi Gross, Moshav Mazor (IL)

(73) Assignee: Visioncare Ophthalmic Technologies Inc., Saratoga, CA (US)

( * ) Notice: Subject to any disclaimer, the term of this patent is extended or adjusted under 35 U.S.C. 154(b) by 0 days.

(21) Appl. No.: 10/342,160

(22) Filed: Jan. 14, 2003

(65) Prior Publication Data

US 2004/0138746 A1 Jul. 15, 2004

(51) Int. Cl.[7] .............................................. A61F 2/16
(52) U.S. Cl. ................................. 623/6.34; 623/6.15
(58) Field of Search ........................ 623/6.13, 6.15, 623/6.31, 6.32, 6.34, 6.35, 6.37, 6.62

(56) References Cited

U.S. PATENT DOCUMENTS

| | | | |
|---|---|---|---|
| 4,892,543 A * | 1/1990 | Turley .......................... | 623/6.13 |
| 5,222,981 A | 6/1993 | Werblin | |
| 5,384,606 A * | 1/1995 | Koch et al. .................. | 351/158 |
| 5,391,202 A * | 2/1995 | Lipshitz et al. .............. | 623/6.34 |
| 5,628,798 A | 5/1997 | Eggleston et al. | |
| 5,653,751 A | 8/1997 | Samiy et al. | |
| 5,814,103 A * | 9/1998 | Lipshitz et al. .............. | 623/6.34 |
| 5,876,442 A * | 3/1999 | Lipshitz et al. .............. | 623/6.34 |
| 5,928,283 A * | 7/1999 | Gross et al. .................. | 623/6.34 |
| 6,007,579 A * | 12/1999 | Lipshitz et al. .............. | 623/6.11 |
| 6,066,171 A * | 5/2000 | Lipshitz et al. .............. | 623/6.18 |
| 6,464,725 B2 * | 10/2002 | Skotton ........................ | 623/6.34 |
| 6,596,026 B1 * | 7/2003 | Gross et al. .................. | 623/6.34 |
| 2004/0117011 A1 | 6/2004 | Aharoni et al. | |

FOREIGN PATENT DOCUMENTS

| | | |
|---|---|---|
| DE | 34 28 895 A1 | 2/1986 |
| DE | 195 01 444 A1 | 7/1996 |
| EP | 0 897 702 A2 | 2/1999 |
| WO | WO-83/01566 A1 | 5/1983 |
| WO | WO-94/07435 A1 | 4/1994 |
| WO | WO-00/38593 A1 | 7/2000 |

OTHER PUBLICATIONS

Aharoni et al., U.S. Appl. No. 10/498,388, entitled Interacular Implants.

* cited by examiner

*Primary Examiner*—Paul B. Prebilic
(74) *Attorney, Agent, or Firm*—Darby & Darby

(57) ABSTRACT

An intraocular lens implant particularly suitable for use by patients suffering from tunnel vision, the implant includes a sealed implant housing associated with mounting haptics and defining a forward end and a rearward end, at least one negative lens arranged adjacent the forward end and at least one positive lens arranged rearwardly of the at least one negative lens.

14 Claims, 4 Drawing Sheets

INTRAOCULAR LENS IMPLANT

FIELD OF THE INVENTION

The present invention relates to optical implants generally and more particularly to intraocular lens implants for patients suffering from tunnel vision.

BACKGROUND OF THE INVENTION

The following U.S. patents of the inventor are believed to represent the current state of the art:
U.S. Pat. Nos. 5,814,103; 5,876,442; 5,928,283; 6,007,579 and 6,066,171.

SUMMARY OF THE INVENTION

The present invention seeks to provide an optical implant suitable for alleviating the tunnel vision symptom characteristic of glaucoma and retinosis pigmentosa.

There is thus provided in accordance with a preferred embodiment of the present invention an intraocular lens implant particularly suitable for use by patients suffering from tunnel vision. The implant includes a sealed implant housing associated with mounting haptics and defining a forward end and a rearward end, at least one negative lens arranged adjacent the forward end and at least one positive lens arranged rearwardly of the negative lens.

Further in accordance with a preferred embodiment of the present invention the positive lens forms a rearward window of the sealed implant housing.

Additionally in accordance with a preferred embodiment of the present invention at least one air gap is defined within the sealed implant housing. Preferably two air gaps are provided and include a first air gap disposed between the negative lens and the forward end of the sealed implant housing and a second air gap disposed between the negative lens and the positive lens.

Still further in accordance with a preferred embodiment of the present invention the positive lens includes first and second positive lenses, which contact each other at a contact location.

Preferably, an air gap is defined between portions of the first and second positive lenses surrounding the contact location.

Further in accordance with a preferred embodiment of the present invention, the intraocular lens implant also includes a resilient element disposed within the sealed implant housing in operative engagement with the first and second positive lenses, thereby urging the first and second positive lenses into contact at the contact location.

Still further in accordance with a preferred embodiment of the present invention the sealed housing includes a glass housing, which is sealed by glass laser.

Additionally in accordance with a preferred embodiment of the present invention the surfaces of the positive lens and the negative lens, which lie within the sealed housing, are coated with optical coatings.

Preferably, the negative lens and the positive lens include at least one of refractive and diffractive optical elements.

Further in accordance with a preferred embodiment of the present invention the intraocular lens implant is in operative association with at least one negative lens disposed outside an eye in which the implant is located.

Preferably, the sealed implant housing includes a generally annular element, which is sealed to a window at the forward end.

Further in accordance with a preferred embodiment of the present invention the sealed implant housing includes first and second generally cylindrical portions sealed together in a nesting arrangement, thereby defining a shoulder.

Still further in accordance with a preferred embodiment of the present invention the first positive lens is sealed to one of the first and second cylindrical portions at the rearward end to define a rearward window.

Additionally in accordance with a preferred embodiment of the present invention the first positive lens defines a rearward window of the sealed implant housing.

Further in accordance with a preferred embodiment of the present invention the negative lens and the second positive lens define a doublet having an air gap therebetween.

Preferably, the negative lens and the second positive lens define a doublet having an air gap therebetween and are fixed to each other.

BRIEF DESCRIPTION OF THE DRAWINGS

The present invention will be understood and appreciated more fully from the following detailed description, taken in conjunction with the drawings in which.

DETAILED DESCRIPTION OF A PREFERRED EMBODIMENT

Figure 1:
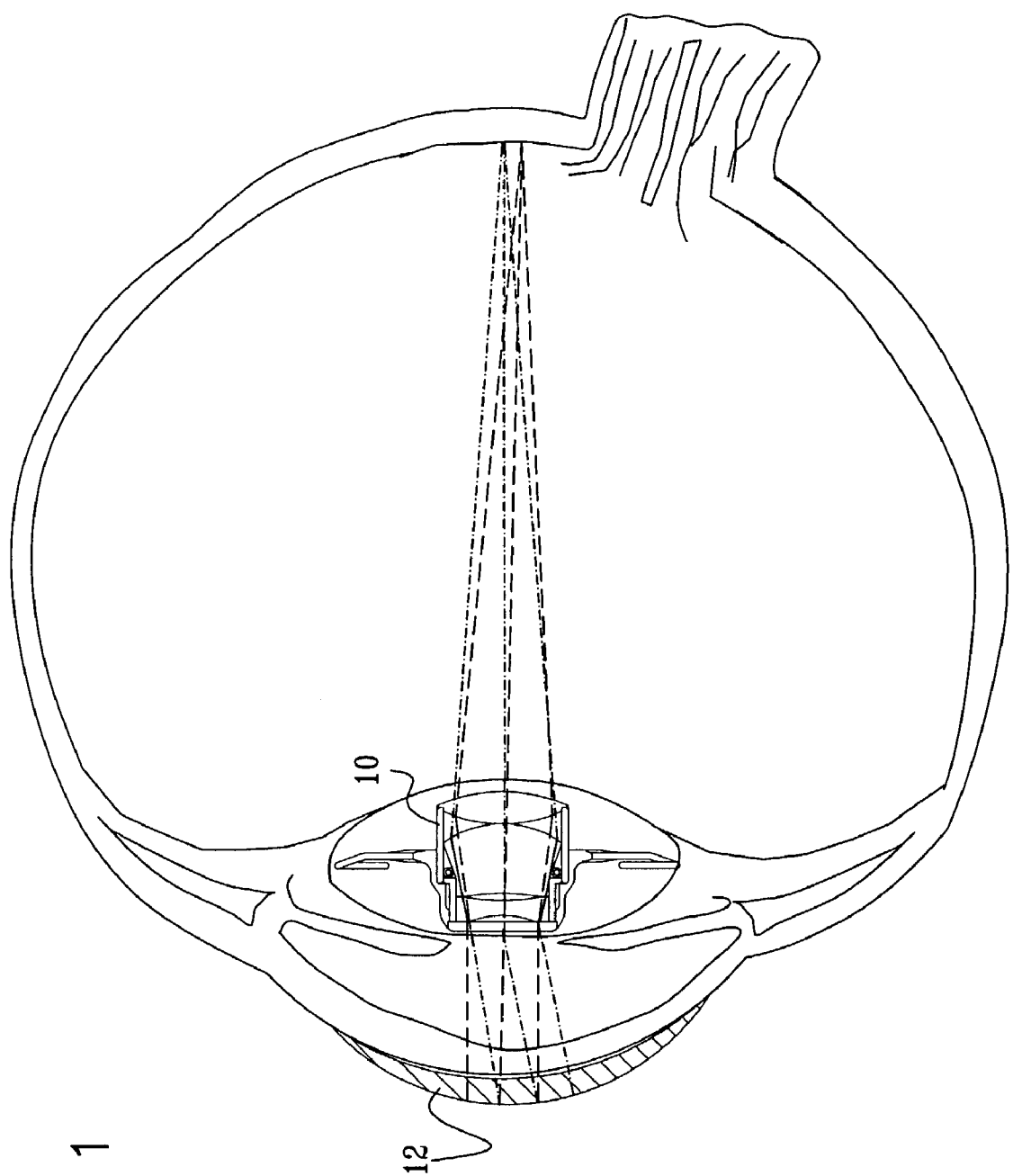
FIG. 1 is a simplified illustration of a field of view widening telescopic implant implanted in the eye of a wearer wearing contact lenses.

Reference is now made to FIG. 1, which is a simplified illustration of a field of view widening telescopic implant 10 implanted in the eye of a wearer wearing a contact lens 12. It is seen that both the contact lens 12 and the implant 10 cooperate to widen the field of view of the user.

Figure 2:
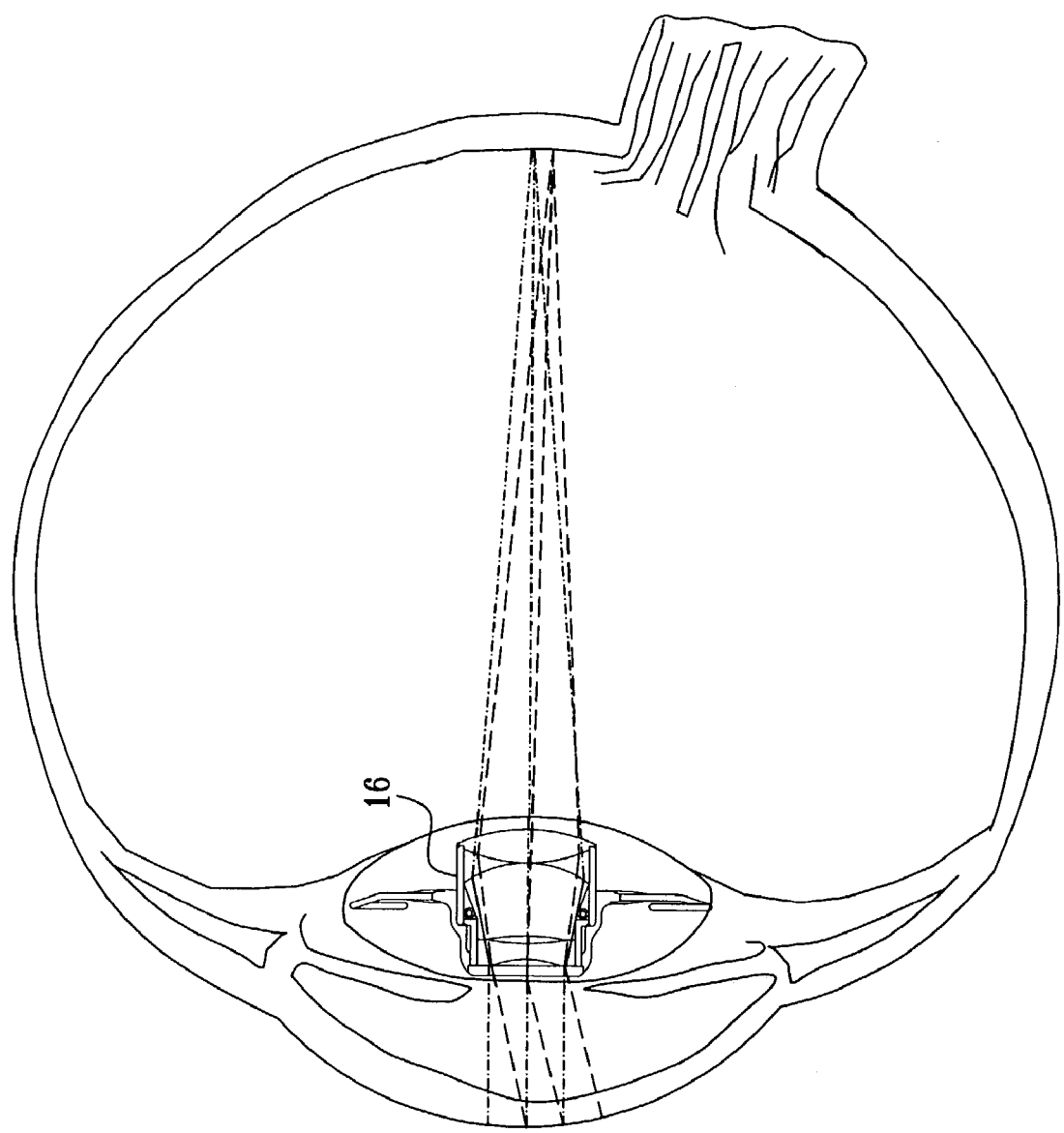
FIG. 2 is a simplified illustration of a field of view widening telescopic implant implanted in the eye of a wearer not wearing glasses or contact lenses.

Reference is now made to FIG. 2, which is a simplified illustration of a field of view widening telescopic implant 16 implanted in the eye of a wearer not wearing glasses or contact lenses. Here the implant 16 is operative to widen the field of view of the user.

Figure 3:
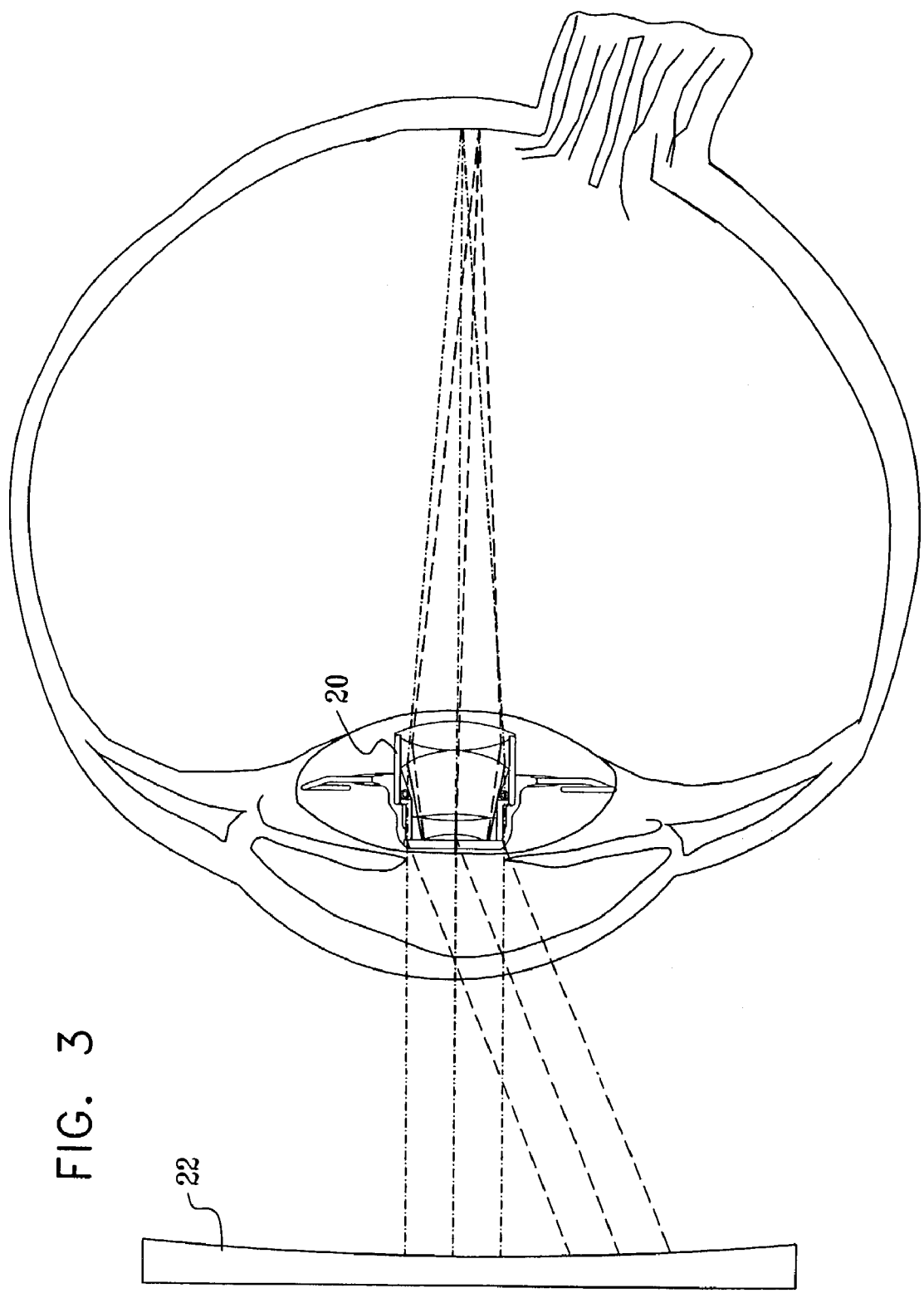
FIG. 3 is a simplified illustration of a field of view widening telescopic implant implanted in the eye of a wearer wearing glasses.

Reference is now made to FIG. 3, which is a simplified illustration of a field of view widening telescopic implant 20 implanted in the eye of a wearer wearing glasses 22. It is seen that both the glasses 22 and the implant 20 cooperate to widen the field of view of the user.

Figure 4:
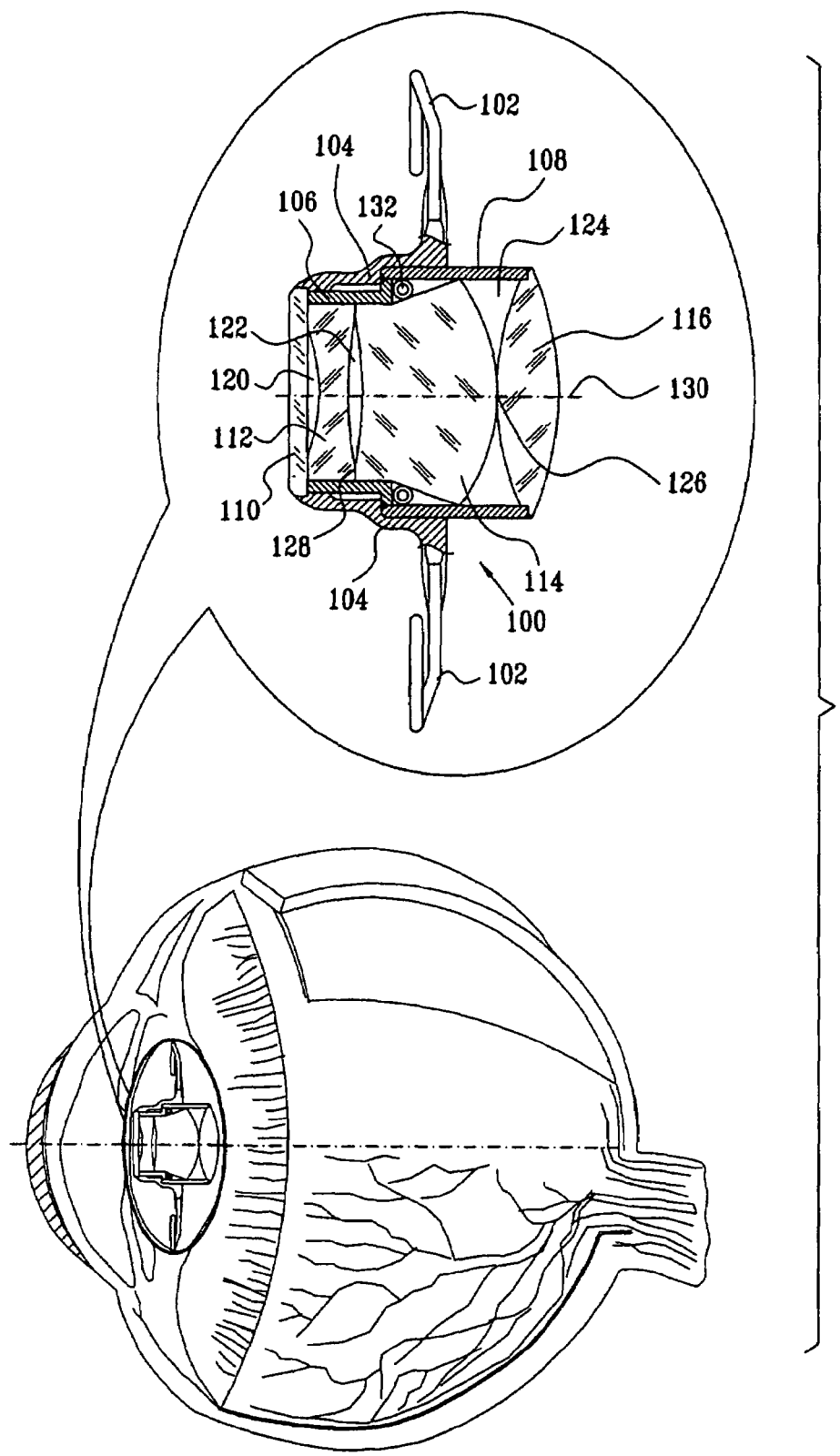
FIG. 4 is a simplified sectional illustration of a field of view widening telescopic implant constructed and operative in accordance with a preferred embodiment of the present invention.

Reference is now made to FIG. 4, which is a simplified sectional illustration of a field of view widening telescopic implant constructed and operative in accordance with a preferred embodiment of the present invention. The embodiment of FIG. 4 can be employed in any of the operational contexts shown in FIGS. 1–3 with suitable selection of lenses. As seen in FIG. 4, the implant preferably comprises an implant body 100, which is supported by haptics 102 via a haptic mounting structure 104. The implant body 100 typically comprises mutually sealed forward and rearward cylindrical housing portions 106 and 108 respectively and a transparent forward window 110 sealing the forward cylindrical portion 106.

Typically, the implant body 100 is formed of glass housing portions, which are sealed by glass laser welding.

Disposed rearwardly of the forward window 110 in forward cylindrical portion 106 is a negative lens 112. Fixed to negative lens 112 as a doublet is a magnification lens 114, which resides partially in the forward cylindrical housing portion 106 and partially in the rearward cylindrical housing portion 108. Disposed rearwardly of the magnification lens 114 is a positive lens 116, which is mounted in sealing engagement with the rearward cylindrical housing portion 108 of implant body 100 and defines a rearward facing window.

Preferably, the negative lens 112 and the positive lens 116 include refractive and diffractive optical elements.

Typically, the negative lens 112 and the positive lens 116 are coated with optical coatings.

It is an important feature of the present invention that the interior of the implant body 100 is sealed from the exterior thereof, so as to prevent liquids or vapors from entering the implant. It is also an important feature of the present invention that three air gaps, designated by reference numerals 120, 122 and 124, are provided to enhance refraction. The precision of the location of a contact point 126 between lenses 114 and 116 and of a peripheral contact area 128 between lenses 112 and 114 relative to an axis 130 is also of importance to maintain desired focus.

In accordance with a preferred embodiment of the present invention, a resilient O-ring 132 or other element having a similar function is provided to urge and retain lenses 114 and 116 in touching engagement at contact point 126.

Alternatively, the implant body may be formed of a single cylinder or of any suitable number of cylindrical portions. Furthermore, any suitable combination of any suitable number of lenses may be employed. Preferably, the haptics 102 are formed of a suitable polymer, the implant body 100 is formed of biocompatible glass and the forward window 110 and the lens 116 are formed of glass and are laser welded in sealing engagement with body 100.

It will be appreciated by persons skilled in the art that the present invention is not limited by what has been particularly shown and described hereinabove. Rather the scope of the present invention includes both combinations and subcombinations of the various features described hereinabove as well as variations and modifications which would occur to persons skilled in the art upon reading the specification and which are not in the prior art.

What is claimed is:

1. An intraocular lens implant particularly suitable for use by patients suffering from tunnel vision, said implant comprising:
   a negative lens having a first diameter;
   a positive lens having a second diameter, said second diameter being greater than said first diameter;
   a magnification lens which contacts said positive lens at a contact location;
   an implant housing associated with mounting haptics and enclosing at least said negative lens, said implant housing having a sealed first end and a second end, said second end being sealed by said positive lens; and
   a resilient element disposed within said implant housing and operative to urge said positive lens and said magnification lens into contact.

2. An intraocular lens implant according to claim 1 and wherein at least one air gap is defined within said implant housing.

3. An intraocular lens implant according to claim 2 and wherein said at least one air gap comprises:
   a first air gap disposed between said negative lens and said first end of said implant housing;
   a second air gap disposed between said negative lens and said positive lens.

4. An intraocular lens implant according to claim 1 and wherein at least one air gap is defined between portions of said positive lens and said magnification lens surrounding said contact location.

5. An intraocular lens implant according to claim 1 and wherein said housing comprises a glass housing which is sealed by glass laser welding.

6. An intraocular lens implant according to claim 1 and wherein surfaces of said positive lens and of said at least one negative lens which lie within said sealed housing are coated with optical coatings.

7. An intraocular lens implant according to claim 1 and wherein said negative lens and said positive lens include at least one of refractive and diffractive optical elements.

8. An intraocular lens implant according to claim 1 and being operatively in association with at least one negative lens disposed outside an eye in which the implant is located.

9. An intraocular lens implant according to claim 1 and wherein said implant housing also comprises a generally annular element which is sealed to a window at said forward end.

10. An intraocular lens implant according to claim 9 and wherein said implant housing further includes first and second generally cylindrical portions sealed together in a nesting arrangement thereby defining a shoulder.

11. An intraocular lens implant according to claim 10 and wherein at least one air gap is defined between portions of said positive lense and said magnification lens surrounding said contact location.

12. An intraocular lens implant according to claim 10 and wherein said positive lens is sealed to one of said first and second cylindrical portions at said second end.

13. An intraocular lens implant according to claim 1 and wherein said negative lens and said magnification lens define a doublet having an air gap therebetween.

14. An intraocular lens implant according to claim 10 and wherein said negative lens and said magnification lens define a doublet having an air gap therebetween and are fixed to each other.

* * * * *

UNITED STATES PATENT AND TRADEMARK OFFICE
CERTIFICATE OF CORRECTION

PATENT NO. : 6,972,032 B2
DATED : December 6, 2005
INVENTOR(S) : Eli Aharoni et al.

It is certified that error appears in the above-identified patent and that said Letters Patent is hereby corrected as shown below:

<u>Title page,</u>
Insert Item -- [*] Notice, This Patent is subject to a Terminal Disclaimer --.

Signed and Sealed this

Seventh Day of March, 2006

JON W. DUDAS
*Director of the United States Patent and Trademark Office*